US010751336B2

(12) United States Patent
Zuber

(10) Patent No.: US 10,751,336 B2
(45) Date of Patent: Aug. 25, 2020

(54) FLAVORED NICOTINE POWDER

(71) Applicant: PHILIP MORRIS PRODUCTS S.A., Neuchatel (CH)

(72) Inventor: Gerard Zuber, Froideville (CH)

(73) Assignee: Philip Morris Products S.A., Neuchatel (CH)

( * ) Notice: Subject to any disclaimer, the term of this patent is extended or adjusted under 35 U.S.C. 154(b) by 0 days.

(21) Appl. No.: 16/064,170

(22) PCT Filed: Dec. 8, 2016

(86) PCT No.: PCT/IB2016/057452
§ 371 (c)(1),
(2) Date: Jun. 20, 2018

(87) PCT Pub. No.: WO2017/109625
PCT Pub. Date: Jun. 29, 2017

(65) Prior Publication Data
US 2018/0369225 A1  Dec. 27, 2018

(30) Foreign Application Priority Data

Dec. 24, 2015 (EP) .................................... 15202728

(51) Int. Cl.
| | |
|---|---|
| *A61K 31/465* | (2006.01) |
| *A61K 9/50* | (2006.01) |
| *A61K 47/12* | (2006.01) |
| *A61K 47/18* | (2017.01) |
| *A61M 15/00* | (2006.01) |
| *A61K 9/00* | (2006.01) |
| *A61K 9/14* | (2006.01) |

(52) U.S. Cl.
CPC .......... *A61K 31/465* (2013.01); *A61K 9/0075* (2013.01); *A61K 9/145* (2013.01); *A61K 9/5015* (2013.01); *A61K 47/12* (2013.01); *A61K 47/183* (2013.01); *A61M 15/0011* (2014.02); *A61M 15/0021* (2014.02)

(58) Field of Classification Search
CPC ........ A61K 31/465; A61K 9/50; A61K 47/12; A61K 47/18; A61M 15/00
See application file for complete search history.

(56) References Cited

U.S. PATENT DOCUMENTS

| | | |
|---|---|---|
| 4,735,217 A | 4/1988 | Gerth et al. |
| 5,746,227 A | 5/1998 | Rose et al. |
| 2002/0110529 A1 | 8/2002 | Bechtold-Peters et al. |
| 2008/0241255 A1 | 10/2008 | Rose et al. |
| 2012/0145150 A1 | 6/2012 | Donovan et al. |
| 2014/0088044 A1 | 3/2014 | Rigas et al. |
| 2014/0261488 A1 | 9/2014 | Tucker |
| 2015/0283070 A1 | 10/2015 | Stenzler |

FOREIGN PATENT DOCUMENTS

| | | |
|---|---|---|
| EP | 1430887 A1 | 6/2004 |
| EP | 2 399 637 A1 | 12/2011 |
| GB | 2 461 008 A | 12/2009 |
| WO | WO 91/01656 A1 | 2/1991 |
| WO | WO 2015/166350 A2 | 11/2015 |

OTHER PUBLICATIONS

International Search Report and Written Opinion for PCT/IB2016/057452, issued by the European Patent Office as the International Searching Authority, dated Feb. 15, 2017; 12 pgs.
Hall, R.L., & Oser, B.L. "Recent progress in the consideration of flavor ingredients under the Food Additives Amendment,". 3. *GRAS Substances. Food Technology for Flavoring Extract Manufacturers Association*, 1965:19 (2, Part 2): 151-197.
Hall, R.L., & Oser, B.L., "Recent progress in the consideration of flavoring ingredients under the Food Additives Amendment," 4. *GRAS Substances. Food Technology for Flavoring Extract Manufacturers Association*, 1970: 24 (5), 25-34.
Oser, B.L., & Hall, R.L. "Recent Progress in the Consideration of Flavoring Ingredients under the Food Additives Amendment," 5. *GRAS Substances. Food Technology, for Flavoring Extract Manufacturers Association*, 1972:26 (5), 35-42.
Oser, B.L., & Ford, R.A. "Recent progress in the consideration of flavoring ingredients under the Food Additives Amendment," 6. *GRAS Substances. Food Technology, for Flavoring Extract Manufacturers Association*, 1973a:27 (1), 64-67.
Oser, B.L., & Ford, R.A. "Recent progress in the consideration of flavoring ingredients under the Food Additives Amendment," 7. *GRAS Substances. Food Technology for Flavoring Extract Manufacturers Association*, 1973b: 27 (11), 56-57.
Oser, B.L., & Ford, R.A., "Recent progress in the consideration of flavoring ingredients under the Food Additives Amendment," 8. *GRAS Substances. Food Technology for Flavoring Extract Manufacturers Association*, 1974:28 (9), 76-80.
Oser, B.L., & Ford, R.A., "Recent progress in the consideration of flavoring ingredients under the Food Additives Amendment," 9. *GRAS Substances. Food Technology for Flavoring Extract Manufacturers Association*, 1975:29 (8), 70-72.
Oser, B.L., & Ford, R.A. "Recent progress in the consideration of flavoring ingredients under the Food Additives Amendment," 10. *GRAS Substances. Food Technology for Flavoring Extract Manufacturers Association*, 1977;31 (1), 65-74.

(Continued)

*Primary Examiner* — Zohreh A Fay
(74) *Attorney, Agent, or Firm* — Mueting Raasch Group

(57) ABSTRACT

A nicotine powder inhaler (10) comprises a body extending between a mouthpiece portion (12) and a distal end portion (14), an airflow channel (15) extending between the mouthpiece portion and the distal end portion and a nicotine powder receptacle (20) disposed along the airflow channel, and a powder system disposed within the nicotine powder receptacle. The powder system includes a first plurality of particles having a particle size of about (10) micrometres or less and including nicotine and a second plurality of particles having a particle size of about 20 micrometres of greater and including flavour. The first plurality of particles comprise an amino acid or nicotine selected from the group consisting of nicotine pyruvate, nicotine mono-pyruvate, nicotine aspartate and nicotine lactate.

20 Claims, 2 Drawing Sheets

(56) References Cited

OTHER PUBLICATIONS

Figure 1:
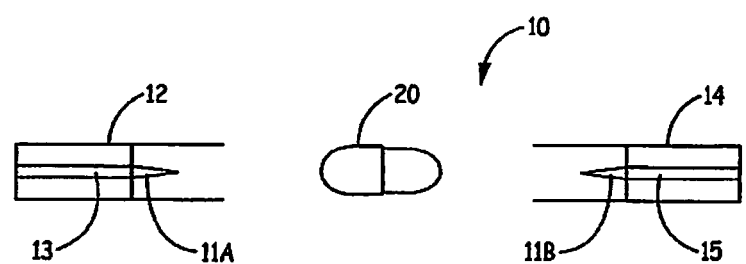

Oser, B.L., & Ford, R.A. "Recent progress in the consideration of flavoring ingredients under the Food Additives Amendment," 11. *GRAS Substances. Food Technology for Flavoring Extract Manufacturers Association*, 1978:32 (2), 60-70.

Oser, B.L., & Ford, R.A. "Recent progress in the consideration of flavoring ingredients under the Food Additives Amendment," 12. *GRAS Substances. Food Technology for Flavoring Extract Manufacturers Association*, 1979:33(7), 65-73.

Oser, B.L., Ford, R.A., & Bernhard, B.K. "Recent progress in the consideration of flavoring ingredients under the Food Additives Amendment," 13. *GRAS Substances. Food Technology for Flavoring Extract Manufacturers Association*, 1984: 38(10), 66-89.

Oser, B. L., Weil, C. S., Woods, L. A., & Bernard, B. K. "Recent progress in the consideration of flavoring ingredients under the food additives amendment," 14. *GRAS Substances. Food Technology for Flavoring Extract Manufacturers Association*, 1985:39(11), 108-117.

Burdock, et al., "Recent progress in the consideration of flavor ingredients under the Food Additives Amendment," 15. *GRAS Substances. Food Technology for Flavoring Extract Manufacturers Association*, 1990:44, 78-86.

Smith, R.L., & Ford, R.A. "Recent progress in consideration of flavoring ingredients under the Food Additives Amendment," 16. *GRAS Substances. Food Technology for Flavoring Extract Manufacturers Association*, 1993:47(6), 104-117.

Smith et al., "GRAS Flavoring Substances 17," *GRAS Flavoring Substances. Food Technology for Flavoring Extract Manufacturers Association*, 1996a:50 (10), 72-78, 80-81.

Newberne et al., "GRAS Flavoring Substances 18," *GRAS Flavoring Substances. Food Technology for Flavoring Extract Manufacturers Association*, 1998:52 (9), 65-92.

Newberne et al., "GRAS Flavoring Substances 19," *GRAS Flavoring Substances. Food Technology for Flavoring Extract Manufacturers Association*, 2000:54(6) 66-68, 70, 72-74, 76-84.

Smith et al., "GRAS Flavoring Substances 20," *GRAS Flavoring Substances. Food Technology for Flavoring Extract Manufacturers Association*, 2001:55(12), 34-55.

Smith et al., "GRAS Flavoring Substances 21," *GRAS Flavoring Substances. Food Technology for Flavoring Extract Manufacturers Association*, 2003;57(5), 46-59.

Smith et al., "GRAS Flavoring Substances 22," *GRAS Flavoring Substances. Food Technology for Flavoring Extract Manufacturers Association*, 2005; 59 (8), 24-62.

Waddell et al., "GRAS Flavoring Substances 23," *GRAS Flavoring Substances. Food Technology for Flavoring Extract Manufacturers Association*, 2007;61(8) 22-61.

Smith et al., "GRAS 24: The 24th publication by the FEMA Expert Panel presents safety and usage data on 236 new generally recognized as safe flavoring ingredients," *Food Technology for Flavoring Extract Manufacturers Association*, 2009; 63(6), 46-105.

Smith et al., "GRAS Flavoring Substances 25: The 25th publication by the Expert Panel of the Flavor and Extract Manufacturers Association provides an update on recent progress in the consideration of flavoring ingredients generally recognized as safe under the Food Additive Amendment," *Food Technology for Flavoring Extract Manufacturers Association*, 2011;65(7), 44-75.

Marnett et al., "GRAS Flavoring Substances 26: The 26th publication by the Expert Panel of the Flavor and Extract Manufacturers Association provides an update on recent progress in the consideration of flavoring ingredients generally recognized as safe under the Food Additive Amendment," *Food Technology for Flavoring Extract Manufacturers Association*, 2013;67(8), 38-56.

Cohen et al., "GRAS Flavoring Substances," 27. *GRAS Flavoring Substances. Food Technology for Flavoring Extract Manufacturers Association*, 2015:69(8):40-59.

Russian Office Action for RU 2018126872 issued by the Russian Patent Office on Mar. 19, 2020;18 pages including English Translation.

FLAVORED NICOTINE POWDER

This application is the § 371 U.S. National Stage of International Application No. PCT/IB2016/057452, filed 8 Dec. 2016, which claims the benefit of EP Patent Application No. 15202728.0, filed 24 Dec. 2015, the disclosures of which are incorporated by reference herein in their entireties.

This disclosure relates to powder systems that include particles comprising nicotine and particles containing flavour, where the flavour particles are larger than the nicotine particles.

Dry powder inhalers (DPI) are known and are used to treat respiratory diseases by delivering a dry powder comprising a pharmaceutical, in aerosol form through inhalation to the patients' airways. For delivery into the lungs, particles in the range of 1 to 5 micrometers are preferred. In pharmaceutical dry powders, the active pharmaceutical ingredient (API) may be agglomerated on the surface of larger carrier particles, such as lactose. DPI's operate complex mechanisms to ensure such agglomerates disperse, break up or disaggregate before the API can be inhaled into the lungs. Pharmaceutical dry powders containing lactose as a carrier can be in the range of 20 to 100 micrometers.

DPI's rely on the force of the patients' inhalation to entrain the powder from the device to subsequently break-up the powder into particles that are small enough to enter the lungs. Sufficiently high inhalation rates are required to ascertain correct dosing and complete disaggregation of the powder. Typically a large amount of API remains attached on the surface of the carrier and is deposited in the upper airways due to incomplete de-aggregation of the powder. Inhalation rates of existing DPI's are usually in the range of 20-100 liters/min (L/min). Existing DPI's are therefore only suitable for delivering dry powders to users in a manner that is different from the inhalation rate associated with smoking articles.

It would be desirable to provide a stable powder system that provides nicotine particles to the lungs of a user and flavour particles to preferably the buccal or mouth cavity of a user. It is desirable that the relative particle sizes of the nicotine and the flavour remain stable even when combined with each other. It is desirable to deliver this stable powder system to a user at inhalation or air flow rates that are within conventional smoking regime inhalation or air flow rates.

A powder system includes a first plurality of particles having a particle size of about 10 micrometres or less and comprising nicotine and a second plurality of particles having a particle size of about 20 micrometres of greater and comprising flavour. The first plurality of particles comprise an amino acid or nicotine selected from the group consisting of nicotine pyruvate, nicotine mono-pyruvate, nicotine aspartate and nicotine lactate. The particles of the powder system are preferably free-flowing.

The powder system may have at least about 40% by weight of the nicotine of the powder system comprised in particles having a particle size of about 10 micrometres or less. The powder system may have at least about 60% by weight of the nicotine of the powder system comprised in particles having a particle size of about 10 micrometres or less. The powder system may have at least about 80% by weight of the nicotine of the powder system comprised in particles having a particle size of about 10 micrometres or less. The powder system may have at least about 90% by weight of the nicotine of the powder system comprised in particles having a particle size of about 10 micrometres or less.

The powder system may have at least about 40% by weight of the nicotine of the powder system comprised in particles having a particle size of about 5 micrometres or less. The powder system may have at least about 60% by weight of the nicotine of the powder system comprised in particles having a particle size of about 5 micrometres or less. The powder system may have at least about 80% by weight of the nicotine of the powder system comprised in particles having a particle size of about 5 micrometres or less. The powder system may have at least about 90% by weight of the nicotine of the powder system comprised in particles having a particle size of about 5 micrometres or less.

The powder system may have at least about 40% by weight of the nicotine of the powder system comprised in particles having a particle size of from about 1 micrometre to about 3 micrometres or less. The powder system may have at least about 60% by weight of the nicotine of the powder system comprised in particles having a particle size of from about 1 micrometre to about 3 micrometres or less. The powder system may have at least about 80% by weight of the nicotine of the powder system comprised in particles having a particle size of from about 1 micrometre to about 3 micrometres or less. The powder system may have at least about 90% by weight of the nicotine of the powder system comprised in particles having a particle size of from about 1 micrometre to about 3 micrometres or less.

The powder system may have at least about 60%, or at least 80%, by weight of the flavour of the powder system comprised in particles having a particle size of about 20 micrometres or more. The powder system may have at least about 60%, or at least 80%, by weight of the flavour of the powder system comprised in particles having a particle size of about 50 micrometres or more. The powder system may have at least about 60%, or at least 80%, by weight of the flavour of the powder system comprised in particles having a particle size of about 150 micrometres or less.

The powder system may comprise from about 50% wt to about 99% wt of the first plurality of particles. The powder system may comprise from about 1% wt to about 50% wt of the second plurality of particles.

The size of a particle, stated herein, preferably refers to the aerodynamic diameter of the particle. The aerodynamic diameter of a powder system is preferably measured with a cascade impactor.

Advantageously, the powder system described herein provides a stable, free flowing powder system that delivers nicotine selectively to the user's lungs and flavour selectively to the user's mouth. Advantageously, the powder system described herein preferably possesses a stable relative particle size of each powder component even when the nicotine particles and the flavour particles are combined. Advantageously, an inhaler utilizing this powder system may not need to reduce a size of the powder particles and may deliver the powder system at inhalation or air flow rates that are within conventional smoking regime inhalation or air flow rates.

The term "nicotine" refers to nicotine and nicotine derivatives such as free-base nicotine, nicotine salts and the like.

The term "flavourant" or "flavour" refers to organoleptic compounds, compositions, or materials that alter and are intended to alter the taste or aroma characteristics of nicotine during consumption or inhalation thereof. The term "flavourant" or "flavour" preferably refers to compounds disclosed in the Flavor & Extract Manufacturers Association (FEMA) Flavor Ingredient Library and in particular in the GRAS Flavoring Substances publications 3 to 27. These FEMA Flavor Ingredient Library publications include: GRAS Flavoring Substances 3, Hall, R. L. & Oser, B. L., Food Technology, February 1965 pg 151-197; GRAS Flavoring Substances 4, Hall, R. L. & Oser, B. L., Food Technology, Vol. 24, No. 5 pg 25-34; GRAS Substances 5, Hall, R. L. & Oser, B. L., Food Technology, 1972 pg 25-37; GRAS Substances 6, Oser, B. L. & R. A. Ford, Food Technology, Vol. 27, No. 1, 1973 pg 64-67; GRAS Substances 7, Oser, B. L. & R. A. Ford, Food Technology, Vol. 27, No. 11, 1973 pg 56-57; GRAS Substances 8, Oser, B. L. & R. A. Ford, Food Technology, September 1974 pg 76-80; GRAS Substances 9, Oser, B. L. & R. A. Ford, Food Technology, August 1975 pg 70-72; GRAS Substances 10, Oser, B. L. & R. A. Ford, Food Technology, January 1977 pg 65-74; GRAS Substances 11, Oser, B. L. & R. A. Ford, Food Technology, February 1978 pg 60-70; GRAS Substances 12, Oser, B. L. & R. A. Ford, Food Technology, July 1979 pg 65-73; GRAS Substances 13, Oser, B. L., et al., Food Technology, October 1984 pg 66-89; GRAS Substances 14, Oser, B. L., et al., Food Technology, November 1985 pg 108-117; GRAS Substances 15, Oser, B. L., et al., Food Technology, February 1990 pg 78-86; GRAS Substances 16, Smith, R. L. & Ford, R. A., Food Technology, June 1993 pg 104-117; GRAS Flavoring Substances 17, Smith, et al., Food Technology, October 1996 pg 72-81; GRAS Flavoring Substances 18, Newberne, P., et al., Food Technology, Vol. 52, No. 9, September 1998 pg 68-92; GRAS Flavoring Substances 19, Newberne, P., et al., Food Technology, Vol. 54, No. 6, June 2000 pg 66-84; GRAS Flavoring Substances 20, Smith, R. L., et al., Food Technology, Vol. 55, No. 12, December 2001 pg 34-55; GRAS Flavoring Substances 21, Smith, R. L., et al., Food Technology, Vol. 57, No. 5, May 2003 pg 46-59; GRAS Flavoring Substances 22, Smith, R. L., et al., Food Technology, August 2005 pg 24-62; GRAS Flavoring Substances 23, Waddell, W. J., et al., Food Technology, August 2007 pg 22-48; GRAS Flavoring Substances 24, Smith, R. L., et al., Food Technology, June 2009 pg 46-105; GRAS Flavoring Substances 25, Smith, R. L., et al, Food Technology, July 2011 pg 44-75; GRAS Flavoring Substances 26, Marnett, S. M., et al., Food Technology, August 2013 pg 38-56; and GRAS flavoring substances 27 S. M. Cohen et al., Food Technology August 2015 pg. 40-59. For the purpose of this disclosure, nicotine is not considered as a flavourant or flavour.

This disclosure relates to powder systems that include a particles comprising nicotine and particles comprising flavour. The powder system provides nicotine particles preferentially to the lungs of a user and flavour particles preferentially to the buccal or mouth cavity of a user. The particles comprising nicotine further include an amino acid or nicotine selected from the group consisting of nicotine pyruvate, nicotine mono-pyruvate, nicotine aspartate and nicotine lactate. The relative particle sizes of the particles comprising nicotine and the particles comprising flavour remain stable even when combined with each other.

The particles comprising nicotine may have any useful size distribution for inhalation delivery preferentially into the lungs of a user. The powder system may have at least about 40% or at least about 60%, or at least about 80%, by weight of the nicotine of the powder system comprised in particles having a particle size of about 10 micrometres or less. The powder system may have at least about 40% or at least about 60%, or at least about 80%, by weight of the nicotine of the powder system comprised in particles having a particle size of about 5 micrometres or less. The powder system may have at least about 40% or at least about 60%, or at least about 80%, by weight of the nicotine of the powder system comprised in particles having a particle size in a range from about 1 micrometer to about 3 micrometres.

Preferably the nicotine may be a pharmaceutically acceptable free-base nicotine, or nicotine salt or nicotine salt hydrate. Useful nicotine salts or nicotine salt hydrates include nicotine pyruvate, nicotine citrate, nicotine aspartate, nicotine lactate, nicotine bitartrate, nicotine salicylate, nicotine fumarate, nicotine mono-pyruvate, nicotine glutamate or nicotine hydrochloride, for example. Preferred nicotine salts or nicotine salt hydrates include nicotine pyruvate, nicotine mono-pyruvate, nicotine aspartate or nicotine lactate.

The compound combined with nicotine to form the salt or salt hydrate may be chosen based on its expected pharmacological effect. For example: nicotine salicylate may be administered for fever relief, as an anti-inflammatory or painkiller; nicotine fumarate may be administered to treat multiple sclerosis; and nicotine mono-pyruvate may be administered for treating chronic obstructive pulmonary disease (COPD) or for weight loss.

The particles comprising nicotine may include an amino acid. The amino acid may be disposed on the nicotine or coating at least a portion of the particles comprising nicotine.

Preferably the amino acid may be leucine such as, L-leucine. Providing an amino acid such as L-leucine with the particles comprising nicotine, especially coating the nicotine with the amino acid, may reduce adhesion forces of the particles comprising nicotine and may reduce attraction between nicotine particles and thus reduce agglomeration of nicotine particles. Similarly, adhesion forces to particles comprising flavour may also be reduced, thus agglomeration of nicotine particles with flavour particles is also reduced. The powder system described herein may be a free flowing material and possess a stable relative particle size of each powder component even when the nicotine particles and the flavour particles are combined.

Preferably, the nicotine may be a surface modified nicotine salt where the nicotine salt particle is a coated particle. A preferred coating material is L-leucine. Particularly useful particles comprising nicotine are one or more of L-leucine coated nicotine bitartrate, or L-leucine coated nicotine pyruvate, or L-leucine coated nicotine mono-pyruvate, or L-leucine coated nicotine aspartate, or L-leucine coated nicotine lactate.

Particles having a particle size of about 10 micrometres or less may have at least about 20 wt % nicotine, or at least about 30 wt % nicotine, or at least 40 wt % nicotine, or at least 50 wt % nicotine. Particles having a particle size of about 10 micrometres or less may comprise nicotine in a range from about 20 to about 100 wt % nicotine, or from about 30 to about 90 wt % nicotine.

Particles having a particle size of about 5 micrometres or less may comprise at least about 20 wt % nicotine, or at least about 30 wt % nicotine, or at least 40 wt % nicotine, or at least 50 wt % nicotine. Particles having a particle size of about 5 micrometres or less may comprise nicotine in a range from about 20 to about 100 wt % nicotine, or from about 30 to about 90 wt % nicotine.

The particles comprising flavour may have any useful size distribution for inhalation delivery preferentially into the mouth or buccal cavity of a user.

The powder system may have at least about 40% or at least about 60%, or at least about 80%, by weight of the flavour of the powder system comprised in particles having a particle size of about 20 micrometres or greater. The powder system may have at least about 40% or at least about 60%, or at least about 80%, by weight of the flavour of the powder system comprised in particles having a particle size of about 50 micrometres or greater. The powder system may have at least about 40% or at least about 60%, or at least about 80%, by weight of the flavour of the powder system comprised in particles having a particle size in a range from about 50 micrometer to about 150 micrometres.

Flavourants or flavours may be provided as a solid flavour (at room temperature of about 22 degrees centigrade and one atmosphere pressure) and may include flavour formulations, flavour-containing materials and flavour precursors. The flavourant may include one or more natural flavourants, one or more synthetic flavourants, or a combination of natural and synthetic flavourants. Flavourants as described herein are organoleptic compounds, compositions, or materials that are selected and utilized to alter or are intended to alter the taste or aroma characteristics of the nicotine during consumption or inhalation thereof.

Flavourants or flavours refer to a variety of flavour materials of natural or synthetic origin. They include single compounds and mixtures. Preferably the flavour or flavourant has flavour properties that enhance the experience of the nicotine during consumption. The flavour may be selected to provide an experience similar to that resulting from smoking a combustible smoking article. For example, the flavour or flavourant may enhance flavour properties such as mouth fullness and complexity. Complexity is generally known as the overall balance of the flavour being richer without dominating single sensory attributes. Mouth fullness is described as perception of richness and volume in the mouth and throat of the consumer.

Suitable flavours include, but are not limited to, any natural or synthetic flavour, such as tobacco, smoke, menthol, mint (such as peppermint and spearmint), chocolate, licorice, citrus and other fruit flavours, gamma octalactone, vanillin, ethyl vanillin, breath freshener flavours, spice flavours such as cinnamon, methyl salicylate, linalool, bergamot oil, geranium oil, lemon oil, and ginger oil, and the like.

Other suitable flavours may include flavour compounds selected from the group consisting of an acid, an alcohol, an ester, an aldehyde, a ketone, a pyrazine, combinations or blends thereof and the like. Suitable flavour compounds may be selected, for example, from the group consisting of phenylacetic acid, solanone, megastigmatrienone, 2-heptanone, benzylalcohol, cis-3-hexenyl acetate, valeric acid, valeric aldehyde, ester, terpene, sesquiterpene, nootkatone, maltol, damascenone, pyrazine, lactone, anethole, iso-s valeric acid, combinations thereof, and the like.

Further specific examples of flavours may be found in the current literature, and are well-known to the person skilled in the art of flavouring, i.e. of imparting an odor or taste to a product.

The flavourant may be a high potency flavourant, and may be used and detected at levels that would result in less than 200 parts per million in inhalation air flow. Examples of such flavourants are key tobacco aroma compounds such as beta-damascenone, 2-ethyl-3,5-dimethylpyrazine, phenylacetaldehyde, guaiacol, and furaneol. Other flavourants may only be sensed by humans at higher concentration levels. These flavourants, which are referred to herein as the lower potency flavourants, are typically used at levels that results in orders of magnitude higher amounts of flavourant released into the inhalation air. Suitable lower potency flavourants include, but are not limited to, natural or synthetic menthol, peppermint, spearmint, coffee, tea, spices (such as cinnamon, clove and ginger), cocoa, vanilla, fruit flavours, chocolate, eucalyptus, geranium, eugenol and linalool.

The particles comprising flavour may include a compound to reduce adhesion forces or surface energy and resulting agglomeration. The flavour particle may be surface modified with an adhesion reducing compound to form a coated flavour particle. One preferred adhesion reducing compound may be magnesium stearate. Providing an adhesion reducing compound such as magnesium stearate with the flavour particle, especially coating the flavour particle, may reduce adhesion forces of the particles comprising flavour and may reduce attraction between flavour particles and thus reduce agglomeration of flavour particles. Thus agglomeration of flavour particles with nicotine particles may also be reduced. The powder system described herein thus may possess a stable relative particle size of the particles comprising nicotine and the particles comprising flavour even when the nicotine particles and the flavour particles are combined. The powder system preferably is free flowing.

The flavour particle may have at least about 10 wt % flavour, or at least about 20 wt % flavour, or at least 30 wt % flavour, or at least 40 wt % flavour. The flavour particle may comprise flavour in a range from about 10 to about 100 wt % flavour, or from about 30 to about 90 wt % flavour.

Conventional formulations for dry powder inhalation typically contain carrier particles that serve to increase the fluidization of the active particles since the active particles may be too small to be influenced by simple airflow though the inhaler. These carrier particles are usually a saccharide such as lactose or mannitol that has a particle size greater than about 50 micrometres. The carrier particles are utilized to improve the dose uniformity by acting as a diluent or bulking agent in a formulation. Carrier particles such as lactose or mannitol are not considered flavourants or flavour material in this disclosure.

The powder system described herein may be carrier-free or substantially free of a saccharide such as lactose or mannitol. Being carrier-free or substantially free of a saccharide such as lactose or mannitol may allow the nicotine and to be inhaled and delivered to the user's lungs at inhalation or airflow rates that are similar to typical smoking regime inhalation or airflow rates. In addition, since the nicotine is carrier-free or substantially free of a saccharide such as lactose or mannitol, the airflow path of the inhaler may have simple geometry or a simple configuration.

The powder system includes particles comprising nicotine and particles comprising flavour. The nicotine particles and the flavour particles may be combined in a single capsule. As described above, the nicotine particles and the flavour particles may each have reduced adhesion forces that result in a stable powder formulation where the particle size of the nicotine particles and the flavour particles does not substantially change when combined. The powder system is preferably free flowing.

Alternatively, the powder system may include the particles comprising nicotine contained within a nicotine or first capsule and the particles comprising flavour contained within a flavour or second capsule. The nicotine capsule and the separate flavour capsule may be in parallel airflow arrangement or fluid connection or in serial airflow arrangement or fluid connection.

The particles comprising nicotine and the particles comprising flavour may be combined in any useful relative amount so that the flavour is detected by the user when consumed with the nicotine. The first plurality of particles comprising nicotine may be from about 50% wt to about 99% wt of the total weight of the powder system and the second plurality of particles comprising flavour may be about 50% wt to about 1% wt of the total weight of the powder system. Preferably, the nicotine particles and the flavour particles form at least about 90% wt, or at least about 95% wt, or at least about 99% wt, or 100% wt of the total weight of the powder system.

The airflow path or airflow channel through the body of the inhaler may be a simple path or channel. Preferably, the airflow path or airflow channel through the body of the inhaler may be parallel to a longitudinal axis of the inhaler and may be linearly extending along an entire length of the inhaler body. The inhaler may have only a single main airflow channel with a single capsule receptacle disposed therein. Alternatively, the inhaler may include two or three co-extensive or parallel airflow channels. One, two or all three of the airflow channels may include a capsule receptacle disposed therein. The inhaler may be configured to deliver the nicotine particles and flavour particles simultaneously.

Preferably, the particles comprising nicotine and the particles comprising flavour may be a dry powder intermixed and within a single capsule. Alternatively, the particles comprising flavour may be separated from the particles comprising nicotine before inhalation or delivery through the airflow channels of the inhaler. The particles comprising nicotine and the particles comprising flavour may be in serial airflow arrangement and disposed within a single airflow channel and the particles comprising flavour may be either upstream or downstream of the particles comprising nicotine. Alternatively, the particles comprising nicotine and the particles comprising flavour may be in parallel airflow arrangement and disposed within a pair of airflow channels where the particles comprising nicotine and the particles comprising flavour combine to form a mixture downstream of both the nicotine receptacle and the flavour receptacle.

The nicotine receptacle may receive a capsule containing the nicotine and optionally the flavour (when combined within a single capsule). The capsule may contain a predetermined amount or dose of nicotine and optional flavour. The capsule may contain enough nicotine to provide at least 2 inhalations or "puffs" of nicotine, or at least about 5 inhalations or "puffs" of nicotine, or at least about 10 inhalations or "puffs" of nicotine. Preferably the capsule may contain enough nicotine to provide from about 5 to 50 inhalations or "puffs" of nicotine, or from about 10 to 30 inhalations or "puffs" of nicotine. Each inhalation or "puff" of nicotine may deliver from about 0.1 mg to about 3 mg of particles comprising nicotine to the lungs of the user or from about 0.2 mg to about 2 mg of nicotine to the lungs of the user or about 1 mg of nicotine to the lungs of the user. Preferably, about 50 to about 150 micrograms of nicotine are delivered to the lungs of the user with each "puff".

The capsule may hold or contain at least about 5 mg of nicotine or at least about 10 mg of nicotine. The capsule may hold or contain less than about 30 mg of nicotine or less than about 25 mg of nicotine, or less than 20 mg of nicotine. Preferably, the capsule holds or contains from about 5 mg to about 30 mg of nicotine or from about 10 mg to about 20 mg of nicotine.

When the particles comprising flavour is blended or combined with the particles comprising nicotine within the capsule, the flavour is present in an amount that provides the desired flavour to each inhalation or "puff" delivered to the user.

The capsule may be formed of an airtight material that may be pierced or punctured by the inhaler. The capsule may formed of a metallic or polymeric material that serves to keep contaminates out of the capsule but may be pierced or punctured by the inhaler during use.

A nicotine powder inhaler includes a body extending between a mouthpiece portion and a distal end portion and an airflow channel extending between the mouthpiece portion and the distal end portion. A nicotine powder receptacle is disposed along the airflow channel and the powder system described herein is disposed within the nicotine powder receptacle.

The powder system may be delivered with a simple inhaler construction at inhalation or air flow rates that are within conventional smoking regime inhalation or air flow rates.

A method of inhaling nicotine into lungs of a user includes inhaling air through the nicotine powder inhaler described herein, at a flow rate of less than about 2 litres per minute to deliver nicotine to the lungs of the user. Flavour may not be delivered to the lungs of the user.

The inhaler may include a piercing element or pair of opposing piercing elements that are configured to pierce the capsule. The piercing element or pair of opposing piercing elements may engage with the capsule of nicotine powder upon loading the capsule of flavour powder into the nicotine powder receptacle or upon demand by an actuator on the body of the inhaler.

The particles comprising flavour may be separated from the particles comprising nicotine and the particles comprising flavour may be contained in a separate capsule. The capsule may be formed of an airtight material that may be pierced or punctured by the inhaler. The capsule may formed of a metallic or polymeric material that serves to keep contaminates out of the capsule but may be pierced or punctured by the inhaler during use.

The nicotine inhaler according to this invention may operate using a flow rate of less than about 5 L/min, or less than about 3 L/min, or less than about 2 L/min or about 1.6 L/min. Preferably, the flow rate is in a range from about 1 L/min to about 3 L/min, or from about 1.5 L/min to about 2.5 L/min. More preferably, the inhalation rate or flow rate is similar to that of Health Canada smoking regime, about 1.6 L/min. In contrast, a conventional DPI operates at a flow rate of about 20-100 L/min or greater, and often requires an energy source or propellant to promote air flow to achieve this air flow rate.

The nicotine inhaler described herein may be used by a consumer like smoking a conventional cigarette or vaping an electronic cigarette. Such smoking or vaping is characterized by two steps: a first step during which a small volume containing the full amount of nicotine desired by the consumer is drawn into the mouth cavity, followed by a second step during which this small volume comprising the nicotine is further diluted by fresh air and drawn deeper into the lungs. Both steps are controlled by the consumer. During the first inhalation step the consumer may determine the amount of nicotine to be inhaled. During the second step, the consumer may determine the volume for diluting the first volume to be drawn deeper into the lungs, maximizing the concentration of active agent delivered to the airway epithelial surface. This smoking mechanism is sometimes called "puff-inhale-exhale".

All scientific and technical terms used herein have meanings commonly used in the art unless otherwise specified. The definitions provided herein are to facilitate understanding of certain terms used frequently herein.

The terms "upstream" and "downstream" refer to relative positions of elements of the inhaler described in relation to the direction of inhalation air flow as it is drawn through the body of the inhaler from a distal end portion to the mouthpiece portion.

As used herein, the singular forms "a", "an", and "the" encompass embodiments having plural referents, unless the content clearly dictates otherwise.

As used herein, "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising," and the like.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure, including the claims.

FIGS. 1-5 are schematic diagrams of illustrative nicotine powder inhalers 10. The schematic drawings are not necessarily to scale and are presented for purposes of illustration and not limitation. The drawings depict one or more aspects described in this disclosure. However, it will be understood that other aspects not depicted in the drawing fall within the scope and spirit of this disclosure.

Figure 2:
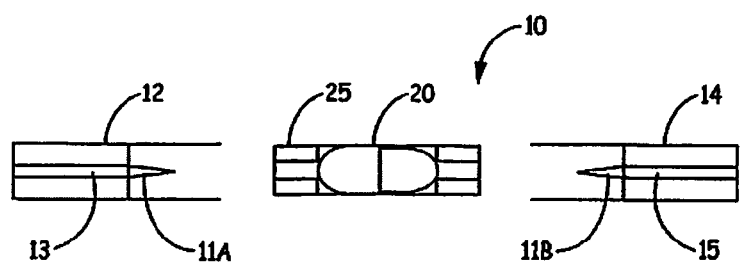

Referring now to FIG. 1 and FIG. 2, the nicotine powder inhalers 10 include a mouthpiece portion 12 and a distal end portion 14 and a nicotine capsule 20 disposed between them. Piercing elements 11A and 11B are configured to pierce the capsule 20 and fluidly connect the airflow channel 13 of the mouthpiece portion 12 with the airflow channel 15 of the distal end portion 14. The airflow channel extends linearly along a length of the nicotine powder inhaler 10. FIG. 2 further illustrates the capsule 20 within a receptacle 25 that may be re-usable.

Figure 3:
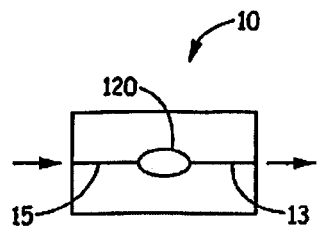
Figure 4:
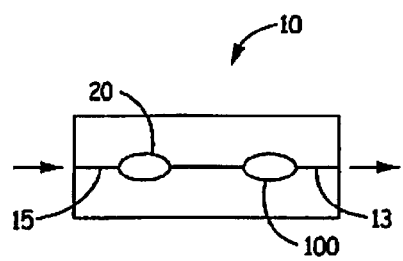
Figure 5:
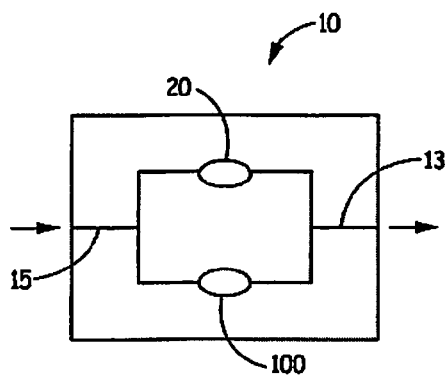

FIGS. 3-5 illustrate schematic diagrams of inhalers 10. FIG. 3 shows a nicotine inhaler 10 having a single flow path and a single capsule 120 containing both the nicotine particles and the flavour particles. The air flow path includes an upstream portion 15 and a downstream portion 13.

FIG. 4 shows a nicotine inhaler 10 having a single flow path and a nicotine capsule 20 containing nicotine particles in serial flow arrangement with the flavourant capsule 100 containing flavour particles. The flavourant capsule 100 may be pierced as described above for the nicotine capsule 20. The air flow path includes an upstream portion 15 and a downstream portion 13.

FIG. 5 shows a nicotine inhaler 10 having a parallel flow path and a nicotine capsule 20 containing nicotine particles in parallel flow arrangement with the flavourant capsule 100 containing flavour particles. The flavourant capsule 100 may be pierced as described above for the nicotine capsule 20. The air flow path includes an upstream portion 15 and a downstream portion 13.

The invention claimed is:

1. A powder system, comprising:
a first plurality of particles having a particle size of about 10 micrometres or less and comprising nicotine and an amino acid; and
a second plurality of particles having a particle size of about 20 micrometres of greater and comprising flavour.

2. A powder system, comprising:
a first plurality of particles having a particle size of about 10 micrometres or less and comprising nicotine and the nicotine selected from the group consisting of nicotine pyruvate, nicotine mono-pyruvate, nicotine aspartate and nicotine lactate; and
a second plurality of particles having a particle size of about 20 micrometres of greater and comprising flavour.

3. The powder system according to claim 1, wherein at least about 60% by weight of the nicotine of the powder system is comprised in particles having a particle size of about 10 micrometres or less.

4. The powder system according to claim 1, wherein at least about 60% by weight of the flavour of the powder system is comprised in particles having a particle size of about 20 micrometres or more.

5. The powder system according to claim 1, wherein the first plurality of particles has a mass median aerodynamic diameter of about 5 micrometres or less, and the second plurality of particles has a mass median aerodynamic diameter of about 50 micrometres or greater.

6. The powder system according to claim 1, wherein the nicotine comprises a nicotine salt or a nicotine salt hydrate.

7. The powder system according to claim 1, wherein the amino acid is disposed on the nicotine.

8. The powder system according to claim 1, wherein the amino acid comprises leucine.

9. The powder system according to claim 1, wherein the first plurality of particles and the second plurality of particles are contained within a single capsule.

10. The powder system according to claim 1, wherein the first plurality of particles is contained within a first capsule and the second plurality of particles is contained within a second capsule.

11. The powder system according to claim 1 wherein the first plurality of particles is from about 50% wt to about 99% wt and the second plurality of particles is about 50% wt to about 1% wt of the total weight of the powder system.

12. The powder system according to claim 1, wherein the second plurality of particles comprises magnesium stearate.

13. A nicotine powder inhaler comprising:
a body extending between a mouthpiece portion and a distal end portion;
an airflow channel extending between the mouthpiece portion and the distal end portion; and
a nicotine powder receptacle disposed along the airflow channel and the powder system of claim 1 disposed within the nicotine powder receptacle.

14. The nicotine powder inhaler of claim 13, wherein the first plurality of particles and the second plurality of particles are contained within a single capsule and the capsule is disposed within the nicotine powder receptacle and the first plurality of particles and the second plurality of particles are released from the single capsule into the airflow channel.

15. The nicotine powder inhaler of claim 13, wherein the first plurality of particles is contained within a first capsule and the second plurality of particles is contained within a second capsule and the second capsule is upstream or downstream of the first capsule and within the airflow channel.

16. The nicotine powder inhaler of claim 13, further comprising a second airflow channel in parallel airflow relation with the nicotine powder receptacle and the first plurality of particles is contained within a first capsule within the nicotine powder receptacle and the second plurality of particles is contained within a second capsule within the second airflow channel.

17. The nicotine powder inhaler according to claim 13, wherein the first plurality of particles are inhaled into lungs of a user at an inhalation rate of less than about 5 litres per minute.

18. A method of inhaling nicotine into lungs of a user, comprising:
   inhaling air through the nicotine powder inhaler according to claim 13, at a flow rate of less than about 2 litres per minute to deliver the first plurality of particles to the lungs of the user and wherein the second plurality of particles is not delivered to the lungs of the user.

19. The powder system according to claim 5, wherein the first plurality of particles and the second plurality of particles are contained within a single capsule.

20. The powder system according to claim 19, wherein the first plurality of particles is from about 50% wt to about 99% wt and the second plurality of particles is about 50% wt to about 1% wt of the total weight of the powder system.

* * * * *